United States Patent
Teuber et al.

(10) Patent No.: US 7,335,777 B2
(45) Date of Patent: Feb. 26, 2008

(54) BENZIMIDAZOLE DERIVATIVES AND THEIR USE FOR MODULATING THE $GABA_A$ RECEPTOR COMPLEX

(75) Inventors: Lene Teuber, Værløe (DK); Janus S. Larsen, Holbæk (DK)

(73) Assignee: Neurosearch A/S, Ballerup (DK)

(*) Notice: Subject to any disclaimer, the term of this patent is extended or adjusted under 35 U.S.C. 154(b) by 76 days.

(21) Appl. No.: 10/546,586

(22) PCT Filed: Apr. 1, 2004

(86) PCT No.: PCT/EP2004/050415

§ 371 (c)(1),
(2), (4) Date: Aug. 19, 2005

(87) PCT Pub. No.: WO2004/087137

PCT Pub. Date: Oct. 14, 2004

(65) Prior Publication Data

US 2006/0148856 A1    Jul. 6, 2006

(30) Foreign Application Priority Data

Apr. 3, 2003   (DK) .............................. 2003 00510

(51) Int. Cl.
*C07D 235/06* (2006.01)
*A61K 31/44* (2006.01)
(52) U.S. Cl. .................... 548/304.7; 514/338
(58) Field of Classification Search ............... 548/304.7
See application file for complete search history.

(56) References Cited

U.S. PATENT DOCUMENTS

| | | | |
|---|---|---|---|
| 5,554,630 A * | 9/1996 | Teuber et al. ............... | 514/338 |
| 5,554,632 A * | 9/1996 | Teuber et al. ............... | 514/338 |
| 6,218,547 B1 | 4/2001 | Teuber et al. | |
| 2002/0193385 A1 | 12/2002 | Hallett et al. | |

FOREIGN PATENT DOCUMENTS

| | | |
|---|---|---|
| EP | 0 616 807 A1 | 9/1994 |
| WO | WO-96/33191 A1 | 10/1996 |
| WO | WO-96/33192 A1 | 10/1996 |
| WO | WO-96/33194 A1 | 10/1996 |
| WO | WO-98/17651 A1 | 4/1998 |
| WO | WO-98/34923 A1 | 8/1998 |
| WO | WO-00/78728 A1 | 12/2000 |

OTHER PUBLICATIONS

Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the internet, URL: http:www.cnn.com/2003/HEALTH/conditions/09/24/alzheimers.drug.ap/index.html>.*
Cognitive disorder [online], [retrieved on Sep. 1, 2006 ]. Retrieved from the Internet, URL; http://en.wikipedia.org/wiki/Category:Cognitive_disorders>.*
Vomiting [online], [retrieved on Dec. 14, 2006]. Retrieved from the Internet, URL; http://en.wikipedia.org/wiki/Emesis>.*
Isomers [online], [retrieved on Dec. 14, 2006]. Retrieved from the Internet, URL; http://chemed.chem.purdue.edu/genchem/topicreview/bp/1organic/isomers.html>.*

* cited by examiner

*Primary Examiner*—Rebecca Anderson
*Assistant Examiner*—Shawquia Young
(74) *Attorney, Agent, or Firm*—Birch, Stewart, Kolasch & Birch, LLP

(57) ABSTRACT

This invention relates to novel benzimidazole derivatives of formula (I), pharmaceutical compositions containing these compounds, and methods of treatment therewith. The compounds of the invention are useful in the treatment of central nervous system diseases and disorders, which are responsive to modulation of the $GABA_A$ receptor complex, and in particular for combating anxiety and related diseases

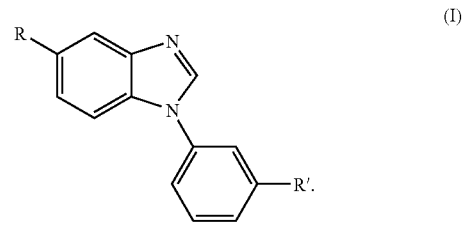

(I)

7 Claims, No Drawings

BENZIMIDAZOLE DERIVATIVES AND THEIR USE FOR MODULATING THE GABA$_A$ RECEPTOR COMPLEX

TECHNICAL FIELD

This invention relates to novel benzimidazole derivatives, pharmaceutical compositions containing these compounds, and methods of treatment therewith.

The compounds of the invention are useful in the treatment of central nervous system diseases and disorders, which are responsive to modulation of the GABA$_A$ receptor complex, and in particular for combating anxiety and related diseases.

BACKGROUND ART

The modulatory sites on the GABA$_A$ receptor complex, such as for example the benzodiazepine receptor, are the targets for anxiolytic drugs, such as the classical anxiolytic benzodiazepines.

Multiple isoforms of the GABA$_A$ receptor exist; each receptor is a pentameric complex comprising subunits drawn from $\alpha_{1-6}$, $\beta_{1-3}$, $\gamma_{1-3}$, $\delta$, $\epsilon$, and $\theta$ subunit isoforms. The classical anxiolytic benzodiazepines show no subtype selectivity. It has been suggested that one of the key elements in the disadvantages of the classical benzodiazepanes (such as sedation, dependency, and cognitive impairment) is relates to the $\alpha 1$ subunit of the GABA$_A$ receptors. Thus compounds with selectivity for the $\alpha 2$ and/or $\alpha 3$ subunits over the $\alpha 1$ subunit are expected to have an improved side effect profile.

EP 616807 describes benzimidazole compounds for use as benzodiazepine receptor ligands.

WO 96/33194, WO 96/33191 and WO 96/33192 describe benzimidazole compounds having affinity for the GABA receptor complex.

WO 98/34923 describes phenylbenzimidazole derivatives as ligands for the GABA receptor complex.

WO 98/17651 and WO 00/78728 describe benzimidazole compounds for use as e.g. anaesthetics.

However, there is a continued strong need to find compounds with an optimized pharmacological profile. Furthermore, there is a strong need to find effective compounds without unwanted side effects associated with older compounds.

SUMMARY OF THE INVENTION

In its first aspect, the invention provides a compound of the Formula I:

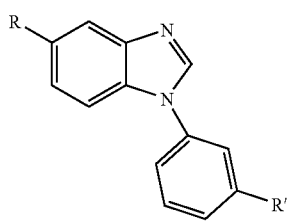

(I)

or an N-oxide thereof, or any of its isomers or any mixture of its isomers, or a pharmaceutically acceptable salt thereof, wherein R and R' are defined as below.

In its second aspect, the invention provides a pharmaceutical composition, comprising a therapeutically effective amount of a compound of the invention, or an N-oxide thereof, or any of its isomers or any mixture of its isomers, or a pharmaceutically acceptable salt thereof, together with at least one pharmaceutically acceptable carrier, excipient or diluent.

In a further aspect, the invention provides the use of a compound of the invention, or an N-oxide thereof, or any of its isomers or any mixture of its isomers, or a pharmaceutically acceptable salt thereof, for the manufacture of a pharmaceutical composition for the treatment, prevention or alleviation of a disease or a disorder or a condition of a mammal, including a human, which disease, disorder or condition is responsive to modulation of the GABA$_A$ receptor complex in the central nervous system.

In a still further aspect, the invention relates to a method for treatment, prevention or alleviation of a disease or a disorder or a condition of a living animal body, including a human, which disorder, disease or condition is responsive to modulation of the GABA$_A$ receptor complex in the central nervous system, which method comprises the step of administering to such a living animal body in need thereof a therapeutically effective amount of a compound of the invention, or an N-oxide thereof, or any of its isomers or any mixture of its isomers, or a pharmaceutically acceptable salt thereof.

Other objects of the invention will be apparent to the person skilled in the art from the following detailed description and examples.

DETAILED DISCLOSURE OF THE INVENTION

Substituted Benzimidazole Derivatives

In its first aspect the present invention provides a compound of general formula (I):

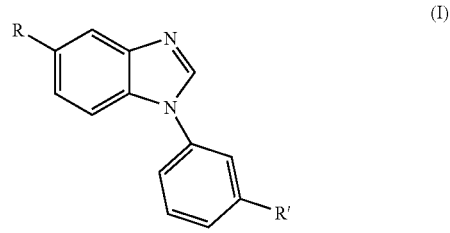

(I)

or an N-oxide thereof, or any of its isomers or any mixture of its isomers, or a pharmaceutically acceptable salt thereof, wherein R represents cycloalkyl; and R' represents a 5-7-membered heterocyclic ring;
  which heterocyclic ring may optionally be substituted one or more substituents independently selected from the group consisting of with halo, hydroxy, amino, alkylamino, aminoalkyl, alkylaminoalkyl, cyano, nitro, trifluoromethyl, trifluoromethoxy, alkoxy, alkoxyalkyl, cycloalkoxy, alkyl, cycloalkyl, cycloalkylalkyl, alkenyl, and alkynyl.

In one embodiment, R represents cyclopropyl or cyclohexyl. In a second embodiment, R represents cyclopropyl. In a third embodiment, R represents cyclohexyl.

In a second embodiment, R' represents a 5-7-membered heterocyclic ring; which heterocyclic ring may optionally be substituted one or more substituents independently selected from the group consisting of with halo, hydroxy, amino, alkylamino, aminoalkyl, cyano, nitro, trifluoromethyl, trifluoromethoxy, alkoxy, cycloalkoxy, alkyl, cycloalkyl, cycloalkylalkyl, alkenyl, and alkynyl In a further embodiment, R' represents a heterocyclic ring selected from the group of pyridyl, thiazolyl, isoxazolyl, imidazolyl, pyrrolyl and pyrazolyl, which heterocyclic ring may optionally be substituted with one or more halo.

In a still further embodiment, R' represents pyridyl optionally substituted with one or more halo. In a special embodiment, R' represents pyridin-3-yl. In a further embodiment, R' represents pyridyl substituted with one halo, such as fluoro. In a special embodiment, R' represent fluoropyridyl, such as 2-fluoro-pyridin-5-yl.

In a further embodiment, R' represents thiazolyl, such as 2-thiazolyl.

In a still further embodiment, R' represents isoxazolyl, such as 3-isoxazolyl.

In a further embodiment, R' represents imidazolyl, such as 1-imidazolyl.

In a still further embodiment, R' represents pyrrolyl, such as 1-pyrrolyl.

In a further embodiment, R' represents pyrazolyl, such as 1-pyrazolyl.

In a still further embodiment, the chemical compound of the invention is an N-oxide of a compound of general formula (I). In a special embodiment, R' represents a pyridyl-N-oxide, such as 3-pyridyl-N-oxide.

In a special embodiment the chemical compound of the invention is
5-Cyclopropyl-1-(3-(3-pyridyl)phenyl)benzimidazole;
5-Cyclopropyl-1-(3-(2-thiazolyl)phenyl)benzimidazole;
5-Cyclopropyl-1-(3-(2-fluoro-5-pyridyl)phenyl)benzimidazole;
5-Cyclopropyl-1-(3-(3-isoxazolyl)phenyl)benzimidazole;
5-Cyclopropyl-1-(3-(1-oxy-3-pyridyl)phenyl)benzimidazole;
5-Cyclohexyl-1-(3-(1-imidazolyl)phenyl)benzimidazole;
5-Cyclohexyl-1-(3-(1-pyrrolyl)phenyl)benzimidazole;
5-Cyclohexyl-1-(3-(1-pyrazolyl)phenyl)benzimidazole;
or an N-oxide thereof, or any of its isomers or any mixture of its isomers,
or a pharmaceutically acceptable salt thereof.

Any combination of two or more of the embodiments as described above is considered within the scope of the present invention.

Definition of Substituents

In the context of this invention halo represents fluoro, chloro, bromo or iodo.

In the context of this invention an alkyl group designates a univalent saturated, straight or branched hydrocarbon chain. The hydrocarbon chain preferably contain of from one to six carbon atoms ($C_{1-6}$-alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In another preferred embodiment of this invention alkyl represents a $C_{1-3}$-alkyl group, which may in particular be methyl, ethyl, propyl or isopropyl.

In the context of this invention an alkenyl group designates a carbon chain containing one or more double bonds, including di-enes, tri-enes and poly-enes. In a preferred embodiment the alkenyl group of the invention comprises of from two to six carbon atoms ($C_{2-6}$-alkenyl), including at least one double bond. In a most preferred embodiment the alkenyl group of the invention is ethenyl; 1- or 2-propenyl; 1-, 2- or 3-butenyl, or 1,3-butdienyl; 1-, 2-, 3-, 4- or 5-hexenyl, or 1,3-hexdienyl, or 1,3,5-hextrienyl.

In the context of this invention an alkynyl group designates a carbon chain containing one or more triple bonds, including di-ynes, tri-ynes and poly-ynes. In a preferred embodiment the alkynyl group of the invention comprises of from two to six carbon atoms ($C_{2-4}$-alkynyl), including at least one triple bond. In its most preferred embodiment the alkynyl group of the invention is ethynyl; 1-, or 2-propynyl; 1-, 2-, or 3-butynyl, or 1,3-butdiynyl; 1-, 2-, 3-, 4-pentynyl, or 1,3-pentdiynyl; 1-, 2-, 3-, 4-, or 5-henynyl, or 1,3-hexdiynyl or 1,3,5-hextriynyl.

In the context of this invention a cycloalkyl group designates a cyclic alkyl group, preferably containing of from three to seven carbon atoms ($C_{3-7}$-cycloalkyl), including cyclopropyl, cyclobutyl, cyclopentyl, cyclohexyl and cycloheptyl.

Alkoxy means O-alkyl, wherein alkyl is as defined above.

Alkoxyalkyl means alkoxy as above and alkyl as above, meaning for example, methoxymethyl.

Cycloalkoxy means O-cycloalkyl, wherein cycloalkyl is as defined above.

Cycloalkylalkyl means cycloalkyl as above and alkyl as above, meaning for example, cyclopropylmethyl.

In the context of this invention alkylamino designates —NH-alkyl or —N-(alkyl)$_2$, wherein alkyl is as defined above.

In the context of this invention a 5-7-membered heterocyclic ring designates a 5-7 membered monocyclic group, and which group holds one or more heteroatoms in its ring structure. Preferred heteroatoms include nitrogen (N), oxygen (O), and sulphur (S). The ring structure may in particular be aromatic (i.e. a heteroaryl), saturated or partially saturated.

Examples of preferred aromatic heterocyclic monocyclic 5-membered groups of the invention include furan, in particular 2- or 3-furyl; thiophene, in particular 2- or 3-thienyl; pyrrole (azole), in particular 1-, 2- or 3-pyrrolyl; oxazole, in particular oxazol-(2-, 4- or 5-)yl; thiazole, in particular thiazol-(2-, 4-, or 5-)yl; imidazole, in particular imidazol-(1-, 2-, 4- or 5-)yl; pyrazole, in particular pyrazol-(1-, 3-, 4- or 5-)yl; isoxazole, in particular isoxazol-(3-, 4- or 5-)yl; isothiazole, in particular isothiazol-(3-, 4- or 5-)yl; 1,2,3-oxadiazole, in particular 1,2,3-oxadiazol-(4- or 5-)yl; 1,2,4-oxadiazole, in particular 1,2,4-oxadiazol-(3- or 5-)yl; 1,2,5-oxadiazole, in particular 1,2,5-oxadiazol-(3- or 4-)yl; 1,3,4-oxadiazole, in particular 1,3,4-oxadiazol-(2- or 5-)yl; 1,2,3-triazole, in particular 1,2,3-triazol-(1-, 4- or 5-)yl; 1,2,4-triazole, in particular 1,2,4-triazol(1-, 3- or 4-)yl; 1,2,4-thiadiazole, in particular 1,2,4-thiadiazol-(3- or 5-)yl; 1,2,5-thiadiazole, in particular 1,2,5-thiadiazol-(3- or 4-)yl; 1,3,4-thiadiazole, in particular 1,3,4-thiadiazol-(2- or 5-)yl; and tetrazole, in particular tetrazol-(1- or 5-)yl.

Examples of preferred saturated or partially saturated heterocyclic monocyclic 5-membered groups of the invention include 1,3-dioxolan, in particular 1,3-dioxolan-(2- or 4-)yl; imidazolidine, in particular imidazolidin-(1-, 2-, 3-, 4- or 5-)yl; 2-imidazoline, in particular 2-imidazolin-(1-, 2-, 4- or 5-)yl; 3-imidazoline, in particular 3-imidazolin-(1-, 2-, 4- or 5-)yl; 4-imidazoline, in particular 4-imidazolin-(1-, 2-, 4- or 5-)yl; dihydro-oxazole (oxazoline), in particular dihydro-oxazol-(2-, 4- or 5-)yl; tetrahydro-oxazole (oxazolidine), in particular tetrahydrooxazol-(2-, 4- or 5-)yl; 1,2,3-oxadiazoline, in particular 1,2,3-oxadiazol-(4- or 5-)yl; 1,2,4-oxadiazoline, in particular 1,2,4-oxadiazolin-(3- or 5-)yl; 1,2,5-oxadiazoline, in particular 1,2,5-oxadiazolin-(3- or 4-)yl; 1,2,3-oxadiazolidine, in particular 1,2,3-oxadiazolidin-(4- or 5-)yl; 1,2,4-oxadiazolidine, in particular 1,2,4-oxadiazolidin-(3- or 5-)yl; 1,2,5-oxadiazolidine, in particular 1,2,5-oxadiazolidin-(3- or 4-)yl; dihydro-pyrrole (pyrroline), in particular dihydro-pyrrol-(1-, 2- or 3-)yl; tetrahydro-pyrrole (pyrrolidine), in particular tetrahydro-pyrrol-(1-, 2- or 3-)yl; pyrazolidine, in particular pyrazolidin-(1-, 2-, 3-, 4- or 5-)yl; 2-pyrazoline, in particular 2-pyrazolin-(1-, 3-, 4- or 5-)yl; and 3-pyrazoline, in particular 3-pyrazolin-(1-, 3-, 4- or 5-)yl.

Examples of preferred aromatic heterocyclic monocyclic 6-membered groups of the invention include pyridine, in particular pyridin-(2-, 3- or 4-)yl; pyridazine, in particular pyridazin-(3- or 4-)yl; pyrimidine, in particular pyrimidin-(2-, 4- or 5-)yl; pyrazine, in particular pyrazin-(2-, 3-, 5- or 6-)yl; 1,3,5-triazine, in particular 1,3,5-triazin-(2-, 4- or 6-)yl; and phosphinine, in particular phosphinin-(2-, 3- or 4-)yl.

Examples of preferred saturated or partially saturated heterocyclic monocyclic 6-membered groups of the invention include 1,4-dioxolane, in particular 1,4-dioxolan-(2- or 3-)yl; 1,4-dithiane, in particular 1,4-dithian-(2- or 3-)yl; morpholine, in particular morpholin-(2-, 3- or 4-)yl; 1,4-oxazine, in particular 1,4-oxazin-(2-)yl; oxadiazine, in particular oxadiazin-(2-, 3- or 5-)yl; piperidine, in particular piperidin-(1-, 2-, 3- or 4-)yl; piperazine, in particular piperazin-(1-, 2-, 3- or 4-)yl; dihydro-pyrane, in particular dihydro-pyran-(2-, 3- or 4-)yl; tetrahydro-pyrane, in particular tetrahydro-pyran-(2-, 3- or 4-)yl; thiomorpholine, in particular thiomorpholin-(2-, 3- or 4-)yl; and 1,3,5-trithiane, in particular 1,3,5-trithian-(2-)yl.

Examples of preferred saturated or partially saturated heterocyclic monocyclic 7-membered groups of the invention include homopiperidine, in particular homopiperidin-(1-, 2-, 3- or 4-)yl; and homopiperazine, in particular homopiperazin-(1-, 2-, 3- or 4-)yl.

Pharmaceutically Acceptable Salts

The chemical compound of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydrochloride derived from hydrochloric acid, the hydrobromide derived from hydrobromic acid, the nitrate derived from nitric acid, the perchlorate derived from perchloric acid, the phosphate derived from phosphoric acid, the sulphate derived from sulphuric acid, the formate derived from formic acid, the acetate derived from acetic acid, the aconate derived from aconitic acid, the ascorbate derived from ascorbic acid, the benzenesulphonate derived from benzensulphonic acid, the benzoate derived from benzoic acid, the cinnamate derived from cinnamic acid, the citrate derived from citric acid, the embonate derived from embonic acid, the enantate derived from enanthic acid, the fumarate derived from fumaric acid, the glutamate derived from glutamic acid, the glycolate derived from glycolic acid, the lactate derived from lactic acid, the maleate derived from maleic acid, the malonate derived from malonic acid, the mandelate derived from mandelic acid, the methanesulphonate derived from methane sulphonic acid, the naphthalene-2-sulphonate derived from naphthalene-2-sulphonic acid, the phthalate derived from phthalic acid, the salicylate derived from salicylic acid, the sorbate derived from sorbic acid, the stearate derived from stearic acid, the succinate derived from succinic acid, the tartrate derived from tartaric acid, the toluene-p-sulphonate derived from p-toluene sulphonic acid, and the like. Such salts may be formed by procedures well known and described in the art. Other acids such as oxalic acid, which may not be considered pharmaceutically acceptable, may be useful in the preparation of salts useful as intermediates in obtaining a chemical compound of the invention and its pharmaceutically acceptable acid addition salt.

Metal salts of a chemical compound of the invention include alkali metal salts such as the sodium salt of a chemical compound of the invention containing a carboxy group.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

Examples of pre- or prodrug forms of the chemical compound of the invention include examples of suitable prodrugs of the substances according to the invention include compounds modified at one or more reactive or derivatizable groups of the parent compound. Of particular interest are compounds modified at a carboxyl group, a hydroxyl group, or an amino group. Examples of suitable derivatives are esters or amides.

The chemical compound of the invention may be provided in dissoluble or indissoluble forms together with a pharmaceutically acceptable solvent such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indissoluble forms for the purposes of this invention.

Steric Isomers

It will be appreciated by those skilled in the art that the compounds of the present invention may contain one or more chiral centres and that such compounds exist in the form of isomers.

The racemates of these isomers and the individual isomers themselves are within the scope of the present invention.

Methods for the resolution of optical isomers, known to those skilled in the art may be used, and will be apparent to the average worker skilled in the art. Such methods include those discussed by J. Jaques, A. Collet, and S. Wilen in "Enantiomers, Racemates, and Resolutions", John Wiley and Sons, New York (1981).

Optical active compounds can also be prepared from optical active starting materials.

N-oxides

In the context of this invention an N-oxide designates an oxide derivative of a ntrogen containing compound, e.g. N-containing heterocyclic compounds capable of forming such N-oxides, and compounds holding one or more amino groups. For example, the N-oxide of a compound containing a pyridyl may be the 1-oxy-pyridin-2, -3 or -4-yl derivative.

N-oxides of the compounds of the invention may be prepared by oxidation of the corresponding nitrogen base using a conventional oxidizing agent such as hydrogen peroxide in the presence of an acid such as acetic acid at an elevated temperature, or by reaction with a peracid such as peracetic acid in a suitable solvent, e.g. dichloromethane, ethyl acetate or methyl acetate, or in chloroform or dichloromethane with 3-chloroperoxybenzoic acid.

Labelled Compounds

The compounds of the invention may be used in their labelled or unlabelled form. In the context of this invention "label" stands for the binding of a marker to the compound of interest that will allow easy quantitative detection of said compound.

The labelled compounds of the invention may be useful as diagnostic tools, radio tracers, or monitoring agents in various diagnostic methods, and for in vivo receptor imaging.

The labelled isomer of the invention preferably contains at least one radionuclide as a label. Positron emitting radionuclides are all candidates for usage. In the context of this invention the radionuclide is preferably selected from $^2$H (deuterium), $^3$H (tritium), $^{13}$C, $^{14}$C, $^{131}$I, $^{125}$I, $^{123}$I, and $^{18}$F.

The physical method for detecting the labelled isomer of the present invention may be selected from Position Emission Tomography (PET), Single Photon Imaging Computed Tomography (SPECT), Magnetic Resonance Spectroscopy (MRS), Magnetic Resonance Imaging (MRI), and Computed Axial X-ray Tomography (CAT), or combinations thereof.

Methods of Preparation

The chemical compounds of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

The compounds of this invention may exist in unsolvated as well as in solvated forms with pharmaceutically acceptable solvents such as water, ethanol and the like. In general, the solvated forms are considered equivalent to the unsolvated forms for the purposes of this invention.

Biological Activity

Compounds of the invention are capable of modulating the $GABA_A$ receptor complex. They may be tested for their ability to bind to the $GABA_A$ receptor complex, including specific subunits thereof.

The compounds of the present invention, being ligands for the benzodiazepine binding site on $GABA_A$ receptors, are therefore of use in the treatment and/or prevention of a variety of disorders of the central nervous system. Thus in further aspect, the compounds of the invention are considered useful for the treatment, prevention or alleviation of a disease, disorder or condition responsive to modulation of the $GABA_A$ receptor complex in the central nervous system.

In a special embodiment, the compounds of the invention are considered useful for the treatment, prevention or alleviation of anxiety disorders, such as panic disorder with or without agoraphobia, agoraphobia without history of panic disorder, animal and other phobias including social phobias, obsessive-compulsive disorder, and generalized or substance-induced anxiety disorder;

stress disorders including post-traumatic and acute stress disorder;

sleep disorders;

memory disorder;

neuroses;

convulsive disorders, for example epilepsy, or febrile convulsions in children;

migraine;

depressive or bipolar disorders, for example single-episode or recurrent major depressive disorder, dysthymic disorder, bipolar I and bipolar II manic disorders, and cyclothymic disorder, psychotic disorders, including schizophrenia;

neurodegeneration arising from cerebral ischemia;

attention deficit hyperactivity disorder;

pain and nociception;

emesis, including acute, delayed and anticipatory emesis, in particular emesis induced by chemotherapy or radiation;

motion sickness, post-operative nausea and vomiting;

eating disorders including anorexia nervosa and bulimia nervosa;

premenstrual syndrome;

muscle spasm or spastcity, e.g. in paraplegic patients;

the effects of substance abuse or dependency, including alcohol withdrawal;

cognitive disorders, such as Alzheimer's disease; and disorders of circadian rhythm, e.g. in subjects suffering from the effects of jet lag or shift work.

Preferably the compounds of the invention are considered useful for the treatment, prevention or alleviation of anxiety disorders, such as panic disorder with or without agoraphobia, agoraphobia without history of panic disorder, animal and other phobias including social phobias, obsessive-compulsive disorder, and generalized or substance-induced anxiety disorder;

Further, the compounds of the invention may be useful as radioligands in assays for detecting compounds capable of binding to the human $GABA_A$ receptor.

Pharmaceutical Compositions

In another aspect the invention provides novel pharmaceutical compositions comprising a therapeutically effective amount of a compound of the invention.

While a compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising a compound of the invention, or a pharmaceutically acceptable salt or derivative thereof, together with one or more pharmaceutically acceptable carriers therefore, and, optionally, other therapeutic and/or prophylactic ingredients, know and used in the art. The carrier(s) must be "acceptable" in the sense of being compatible with the other ingredients of the formulation and not harmful to the recipient thereof.

Pharmaceutical compositions of the invention may be those suitable for oral, rectal, bronchial, nasal, pulmonal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The chemical compound of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The chemical compound of the present invention can be administered in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

For preparing pharmaceutical compositions from a chemical compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid, which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The chemical compound according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations, intended for conversion shortly before use to liquid form preparations for oral administration. Such liquid forms include solutions, suspensions, and emulsions. In addition to the active component such preparations may comprise colorants, flavours, stabilisers, buffers, artificial and natural sweeteners, dispersants, thickeners, solubilizing agents, and the like.

For topical administration to the epidermis the chemical compound of the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantifies of preparation, such as packaged tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration and continuous infusion are preferred compositions.

Further details on techniques for formulation and administration may be found in the latest edition of *Remington's Pharmaceutical Sciences* (Maack Publishing Co., Easton, Pa.).

A therapeutically effective dose refers to that amount of active ingredient, which ameliorates the symptoms or condition. Therapeutic efficacy and toxicity, e.g. $ED_{50}$ and $LD_{50}$, may be determined by standard pharmacological procedures in cell cultures or experimental animals. The dose ratio between therapeutic and toxic effects is the therapeutic index and may be expressed by the ratio $LD_{50}/ED_{50}$. Pharmaceutical compositions exhibiting large therapeutic indexes are preferred.

The dose administered must of course be carefully adjusted to the age, weight and condition of the individual being treated, as well as the route of administration, dosage form and regimen, and the result desired, and the exact dosage should of course be determined by the practitioner.

The actual dosage depend on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Preferred ranges are from about 0.1 µg/kg to about 10 mg/kg/day i.v., and from about 1 µg/kg to about 100 mg/kg/day p.o.

EXAMPLES

The invention is further illustrated with reference to the following examples, which are not intended to be in any way limiting to the scope of the invention as claimed.

Preparation of Intermediates

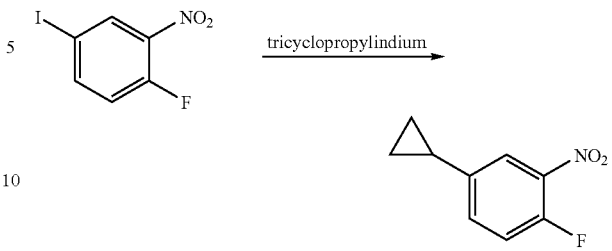

4-Fluoro-3-nitro-1-cyclopropylbenzene was prepared from 2-fluoro-5-iodo-1-nitrobenzene and tricyclopropylindium according to the method described in *J. Am. Chem. Soc.* 2001, 123, 4155-4160.

3-(3-Pyridyl)aniline was prepared as described in WO 96/33191.

3-(2-Fluoro-5-pyridyl)aniline was prepared analogously from 3-nitrophenylboronic acid and 2-fluoro-5-bromopyridine.

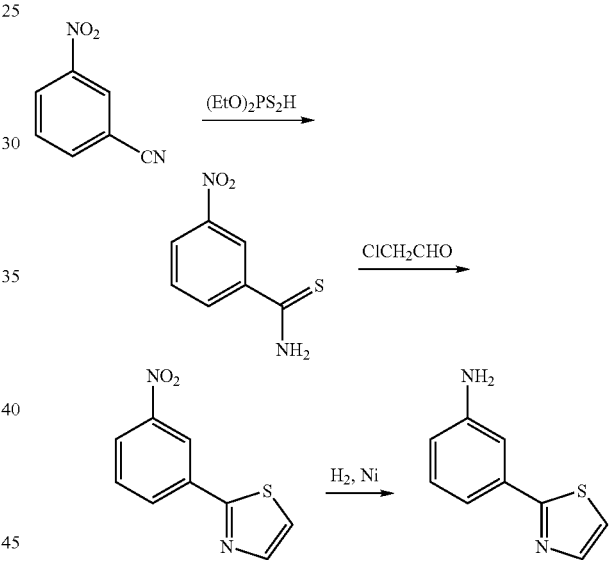

3-Nitro-thio-benzamide. To a stirred solution of 3-nitrobenzonitril (14.5 g, 98 mmol) and diethyl dithiophosphate (16.5 ml, 98 mmol) in ethyl acetate (200 ml) was led gaseous hydrogen chloride. When the evolution of heat had ceased the gas inlet was disconnected and the resultant mixture was left with stirring at ambient temperature over night. Saturated, aqueous sodium carbonate (400 ml) was added, and the layers were separated. The organic layer was dried over magnesium sulphate and concentrated under reduced pressure. The desired product precipitated from the concentrate upon trituration with petroleum ether to afford 17.74 g.

2-(3-Nitrophenyl)thiazole. To a suspension of the above product (17.74 g, 97 mmol) in glacial acetic acid (150 ml) was added chloroacetaldehyde (12.7 ml, 100 mmol) and the resultant mixture was stirred at 125° C. for 2 hours. The cooled mixture was poured into ice-water and rendered alkaline by addition of aqueous sodium hydroxide (12M). Ethyl acetate was added, and the resultant emulsion was filtered through celite prior to separation of the layers. The aqueous layer was extracted 3 times with ethyl acetate, and the combined organic layers were dried over magnesium sulphate and concentrated under reduced pressure. The concentrate was purified by column chromatography on silica gel eluting with a mixture of ethyl acetate and ligroin (1:1 v/v) to afford the desired product (6.6 g).

3-(2-Thiazolyl)aniline. To a suspension of the above product (6.1 g, 29.6 mmol) in ethanol (170 ml) was added Raney nickel (0.5 g) and the resultant mixture was hydrogenated at ambient pressure until the hydrogen uptake had ceased. Filtration through celite and evaporation of the solvent from the filtrate left the desired product, quantitatively.

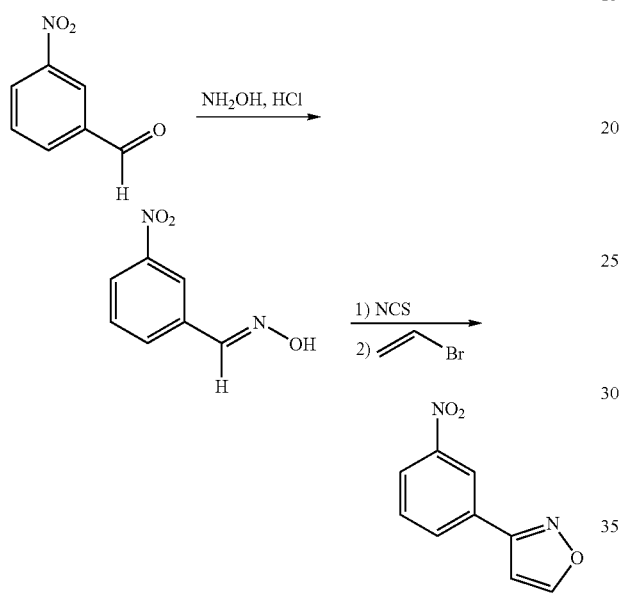

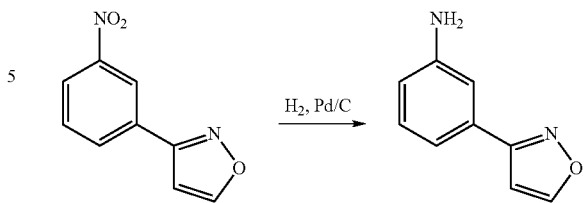

3-(3-Aminophenyl)isoxazole. A suspension of the above product (7.1 g, 37.4 mmol) in abs. ethanol (100 ml) was hydrogenated at ambient pressure, using Pd (5% on activated carbon) as the catalyst, until the hydrogen uptake had ceased. The resultant mixture was filtered through celite and the filtrate was evaporated to leave the desired product as a yellow oil (5.75 g).

Example 1

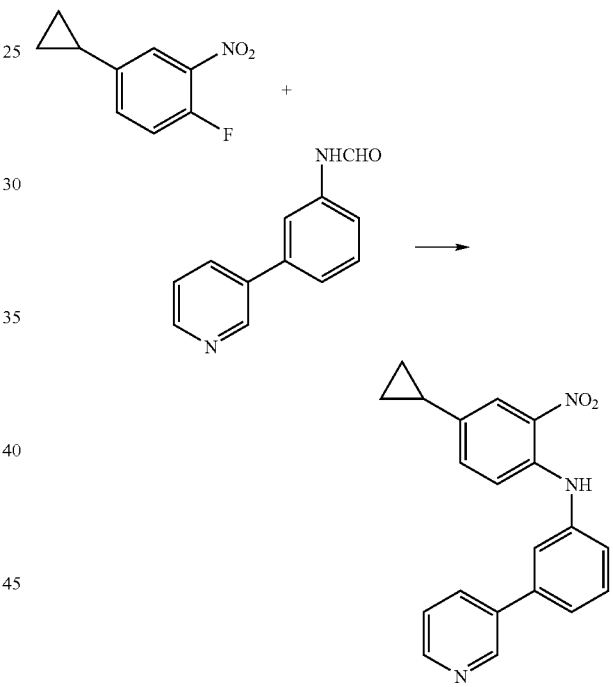

3-Nitrobenzaldehyde oxime. To a suspension of 3-nitrobenzaldehyde (50.5 g, 0.33 mol) in abs. ethanol (500 ml) was added hydroxylamine, hydrochloride (34.89, 0.50 mol) and triethylamine (46.5 ml, 0.33 mol) and the resultant mixture was stirred at reflux over night. The solvent was distilled off under reduced pressure, and water was added to the residue. The resultant solution was rendered alkaline by addition of saturated, aqueous sodium carbonate and the precipitate was filtered off, washed with water and is air-dried to leave the product (51.7 g).

3-(3-Nitrophenyl)isoxazole. To a solution of the above product (10.0 g, 60.2 mmol) in anhydrous dimethyl formamide (500 ml) was added N-chlorosuccinimide (9.6 g, 72.3 mmol) and the resultant mixture was stirred at 60° C. for 3 hours. The mixture was cooled in an ice-bath and vinyl bromide (40 ml, 0.57 mol) was added dropwise. The resultant solution was maintained at 0° C. while a solution of triethyl amine (42 ml, 0.3 mol) in anhydrous dimethyl formamide was added cautiously over 2 hours. After the addition the mixture was stirred at ambient temperature over night. The solvent was distilled off under reduced pressure and the residue was partitioned between water and ethyl acetate. The layers were separated and the organic layer was washed with brine, dried over sodium sulphate and evaporated to dryness. The residue was purified by column chromatography on silica gel using a mixture of ethyl acetate and petroleum ether (1:9, v/v) as the eluent to leave the product (7.1 g).

4-Cyclopropyl-2-nitro-N-(3-(3-pyridyl)phenyl)aniline.
To a solution of N-(3-(3-pyridyl)phenyl)formamide (1.26 g, 6.4 mmol) in anhydrous dimethyl formamide (10 ml) was added sodium hydride (0.82 g 60% dispersion in mineral oil, 6.4 mmol). When the evolution of hydrogen had ceased, 4-fluoro-3-nitrocyclopropylbenzene (0.58 g, 3.2 mmol) was added and the resultant mixture was stirred at room temperature for 2 hours and was then poured into 4 volumes of water. Ethyl acetate was added and the resultant mixture was filtered through celite prior to separation of the layers. The aqueous layer was extracted with ethyl acetate, and the combined organic extracts were washed with aqueous calcium chloride (3M), dried over magnesium sulphate and evaporated to dryness. The residue was purified by column chromatography on silica gel using a mixture of ethyl acetate and petroleum ether (1:1 v/v) as the eluent to afford the desired product (0.5 g).

4-Cyclopropyl-2-nitro-N-(3-(2-thiazolyl)phenyl)aniline was prepared analogously from 4-fluoro-3-nitrocyclopropylbenzene and N-(3-(2-thiazolyl)phenyl)formamide.

4-Cyclopropyl-2-nitro-N-(3-(2-fluoro-5-pyridyl)phenyl) aniline was prepared analogously from 4-fluoro-3-nitro-cyclopropylbenzene and N-(3-(2-fluoro-5-pyridyl)phenyl)formamide.

4-Cyclopropyl-2-nitro-N-(3-(3-isoxazolyl)phenyl)aniline is prepared analogously from 4-fluoro-3-nitrocyclopropylbenzene and N-(3-(3-isoxazolyl)phenyl)formamide.

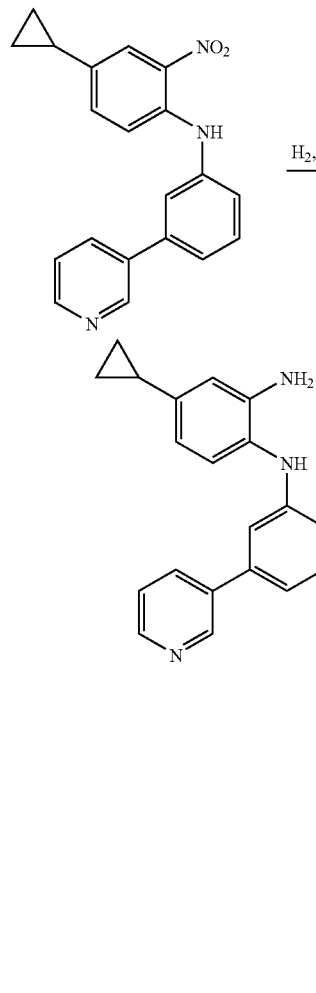

2-Amino-4-cyclopropyl-N-(3-(3-pyridyl)phenyl)aniline was prepared by hydrogenation of 4-cyclopropyl-2-nitro-N-(3-(3-pyridyl)phenyl)aniline in abs. ethanol, using Pd (5% on activated carbon) as the catalyst.

2-Amino-4-cyclopropyl-N-(3-(2-thiazolyl)phenyl)aniline was prepared by hydrogenation of 4-cyclopropyl-2-nitro-N-(3-(2-thiazolyl)phenyl)aniline in abs. ethanol, using Raney nickel as the catalyst.

2-Amino-4-cyclopropyl-N-(3-(2-fluoro-5-pyridyl)phenyl) aniline was prepared by hydrogenation of 4-cyclopropyl-2-nitro-N-(3-(2-fluoro-5-pyridyl)phenyl)aniline in abs. ethanol, using Pd (5% on activated carbon) as the catalyst.

2-Amino-4-cyclopropyl-N-(3-(3-isoxazolyl)phenyl)aniline is prepared by hydrogenation of 4-cyclopropyl-2-nitro-N-(3-(3-isoxazolyl)phenyl)aniline in abs. ethanol, using Pd (5% on activated carbon) as the catalyst.

5-Cyclopropyl-1-(3-(3-pyridyl)phenyl)benzimidazole. To a solution of 2-amino-4-cyclopropyl-N-(3-(3-pyridyl)phenyl)aniline (0.35 g, 1.2 mmol) in tetrahydrofurane (10 ml) was added triethyl orthoformate (0.64 ml, 2.5 mmol) and a catalytic amount of p-toluenesulphonic acid and the resultant mixture was stirred at reflux for 1 hour. The solvent was removed under reduced pressure and the residue was partitioned between water and ethyl acetate. The organic layer was washed with saturated, aqueous sodium carbonate, dried over magnesium sulphate and evaporated to dryness. The desired product crystallised from the residue upon trituration with diethyl ether (0.29 g) Mp 89-90° C.

5-Cyclopropyl-1-(3-(2-thiazolyl)phenyl)benzimidazole was prepared in a similar manner from 2-amino-4-cyclopropyl-N-(3-(2-thiazolyl)phenyl)aniline Mp 75-77° C.

5-Cyclopropyl-1-(3-(2-fluoro-5-pyridyl)phenyl)benzimidazole was prepared in a similar manner from 2-amino-4-cyclopropyl-N-(3-(2-fluoro-5-pyridyl)phenyl)aniline Mp 145-146° C.

5-Cyclopropyl-1-(3-(3-isoxazolyl)phenyl)benzimidazole is prepared in a similar manner from 2-amino-4-cyclopropyl-N-(3-(3-isoxazolyl)phenyl)aniline.

Example 2

As an alternative, 5-cyclopropyl-1-(3-(3-pyridyl)phenyl) benzimidazole was prepared as described below:

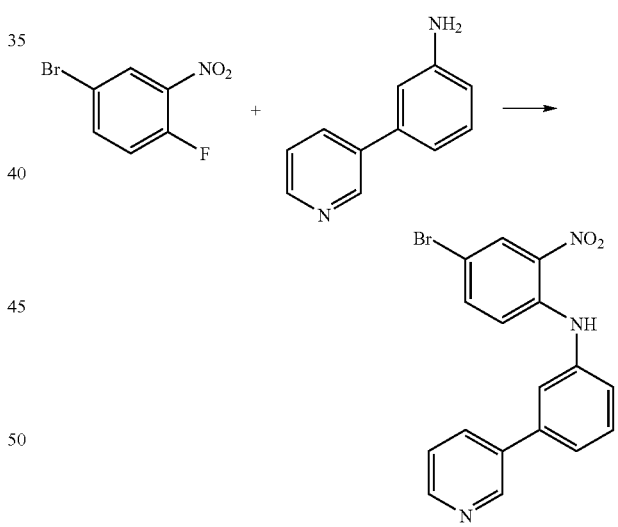

N-(3-(3-pyridyl)phenyl)-4-bromo-2-nitroaniline. To a solution of 1-bromo-4-fluoro-3-nitrobenzene (12.9 g; 58.8 mmol) in anhydrous N-methyl-2-pyrrolidinone (30 ml) was added 3-(3-pyridyl)aniline (10.0 g; 58.8 mmol) and triethylamine (8.2 ml; 58.8 mmol) and the mixture was stirred at 120° C. over night. After cooling the mixture was poured into ice-water (300 ml) and extracted with ethyl acetate. The extract was washed with brine, dried over magnesium sulfate and evaporated under reduced pressure. The residue was purified by column chromatography on silica gel using ethyl acetate as the eluent to yield the reddish product (11.9 g; 55%).

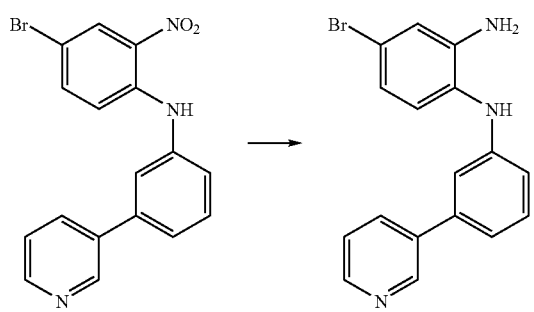

N-(3-(3-pyridyl)phenyl)-2-amino-4-bromoaniline. The above product (11.8 g; 31.9 mmol) was dissolved in a mixture of ethanol (150 ml) and dichloromethane (50 ml) and hydrogenated at ambient pressure, using Raney nickel as the catalyst, until the hydrogen uptake had ceased. The mixture was filtered through filter aid and the filtrate was evaporated to dryness to leave the desired phenylendiamine, quantitatively.

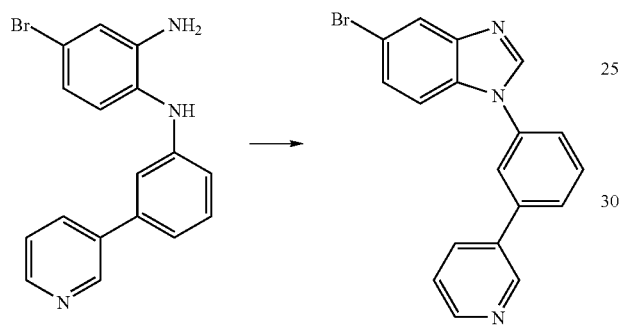

5-Bromo-1-(3-(3-pyridyl)phenyl)benzimidazole. To a solution of the above diamine (10.0 g; 29.4 mmol) in tetrahydrofurane (50 ml) was added triethyl orthoformate (14.7 ml; 88.2 mmol) and a catalytic amount of p-toluensulphonic acid. The mixture was stirred at reflux for 30 min. After cooling water (300 ml) was added and the product was filtered off, washed with water and dried. Yield 8.8 g (85.7%).

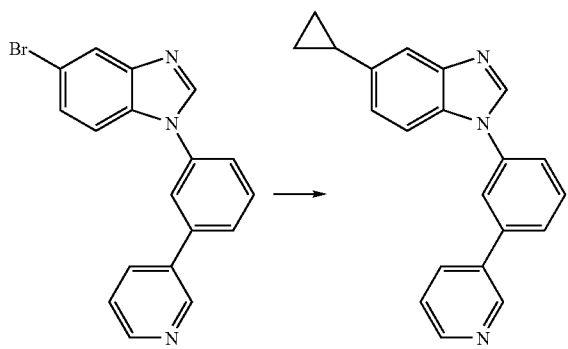

5-Cyclopropyl-1-(3-(3-pyridyl)phenyl)benzimidazole. The cyclopropyl group was introduced as described in *J. Am. Chem. Soc.* 2001, 123, 4155-4160 from the above product and tricyclopropyl indium. The product was purified by preparative LC-MS on an Exterra MS8 column (27 mm×100 mm) using a mixture of A: aqueous formic acid (0.1% v/v) and B: acetonitril as the eluent (gradient: 80% A to 60% A in 13 min.). The product elutes at 8.16 min. Yield: 40%. Mp. 90° C.

Example 3

5-Cyclopropyl-1-(3-(1-oxy-3-pyridyl)phenyl)benzimidazole. To a solution of 5-cyclopropyl-1-(3-(3-pyridyl)phenyl) benzimidazole (0.40 g, 1.3 mmol) in dichloromethane (20 ml) was added m-chloroperbenzoic acid (0.35 g, 1.4 mmol) and the resultant mixture was stirred at room temperature for 2 hours. Saturated, aqueous sodium carbonate was added and the layers were separated. The organic layer was dried over magnesium sulphate and evaporated to dryness. The desired product precipitated from the residue upon trituration with tertbutyl methyl ether (0.27 g) Mp 169-170° C.

Example 4

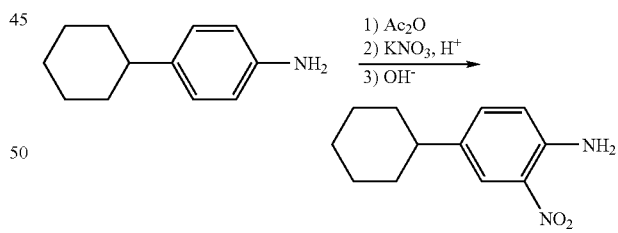

N-(4-Cyclohexyl-2-nitrophenyl)acetamide. A mixture of 4-cyclohexylaniline (10.0 g, 57.1 mmol) and acetic anhydride (50 ml) was stirred at 50° C. for 1 hour. The resultant mixture was cooled in an ice-bath and a solution of potassium nitrate (10.0 g, 99.0 mmol) in conc. sulphuric acid (25 ml) was added drop-wise keeping the temperature at 15-18° C. After the addition, the mixture was poured into ice-water (400 g). The precipitate was filtered off, washed with water and dried. This crude product (12 g) contained a 1:1 mixture of mono- and dinitrated product. The desired product was isolated by column chromatography on silica gel, using a mixture of petroleum ether and ethyl acetate (9:1, v/v) as the eluent (6.5 g).

4-Cyclohexyl-2-nitroaniline. To a solution of the above product (3.5 g, 13.3 mmol) in dimethoxyethane (30 ml) was added aqueous sodium hydroxide (40 ml, 1M). The resultant mixture was stirred at 40° C. over night and was then poured into water (200 ml). The layers were separated and the aqueous layer was extracted with diethyl ether. The combined organic extracts were dried over magnesium sulphate and evaporated under reduced pressure to leave the desired product, quantitatively.

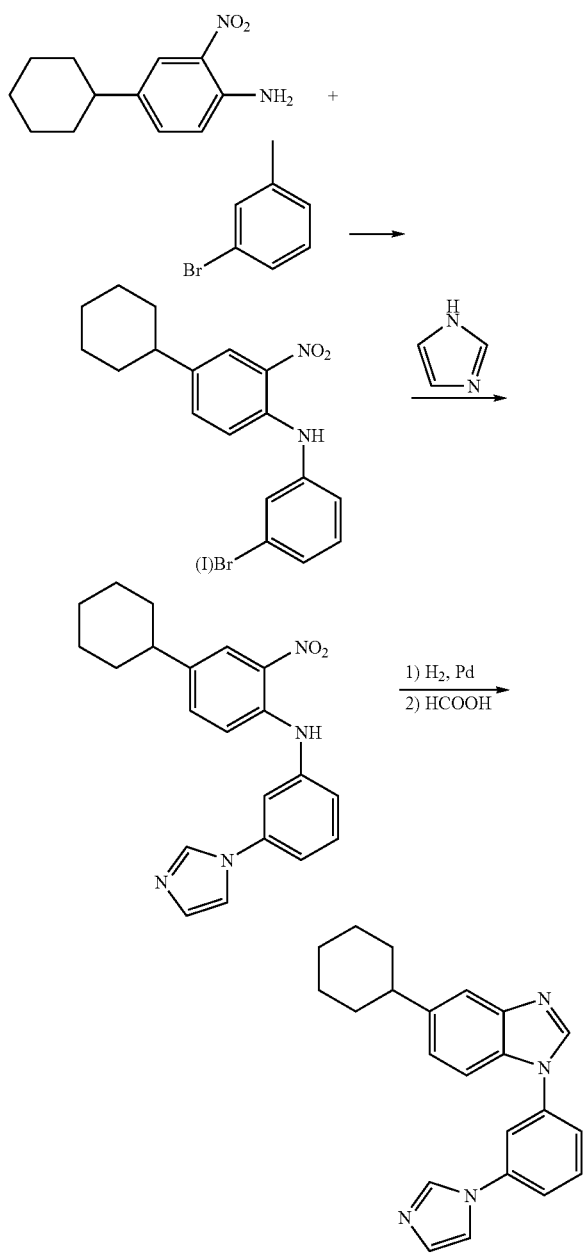

N-(3-Bromophenyl)-4-cyclohexyl-2-nitroaniline. A mixture of the above product (2.1 g, 9.6 mmol), 1-bromo-3-iodobenzene (5.4 g, 19.1 mmol), potassium carbonate (1.4 g, 10 mmol) and a catalytic amount of copper powder was stirred at 200° C. over night. The reaction mixture was cooled to 100° C. and toluene was added. The resultant mixture was stirred at 100° C. for 30 min and was then filtered while hot. The filtrate was concentrated under reduced pressure and the concentrate was eluted through silica gel with a mixture of petroleum ether and ethyl acetate (9:1, v/v) to afford the desired product (0.76 g) in mixture with N-(3-iodophenyl)-4-cyclohexyl-2-nitroaniline.

4-Cyclohexyl-N-(3-(1-imidazolyl)phenyl)-2-nitroaniline. A mixture of the above product (0.76 g), imidazole (0.55 g, 8.1 mmol), potassium carbonate (0.3 g, 2.2 mmol) and a catalytic amount of copper powder was heated to 170° C. for 3 hours. The reaction mixture was cooled to 100° C., water was added and the resultant mixture was allowed to cool to room temperature prior to extraction with diethyl ether. The etheral extract was dried over magnesium sulphate and evaporated under reduced pressure. The residue was purified by column chromatography on silica gel using ethyl acetate as the eluent to afford the desired product (0.25 g).

4-Cyclohexyl-N-(3-(1-pyrrolyl)phenyl)-2-nitroaniline is prepared in a similar manner from N-(3-bromophenyl)-4-cyclohexyl-2-nitroaniline and pyrrole.

4-Cyclohexyl-N-(3-(1-pyrazolyl)phenyl)-2-nitroaniline is prepared in a similar manner from N-(3-bromophenyl)-4-cyclohexyl-2-nitroaniline and pyrazole.

2-Amino-4-cyclohexyl-N-(3-(1-imidazolyl)phenyl)aniline. To a solution of 4-cyclohexyl-N-(3-(1-imidazolyl)phenyl)-2-nitroaniline (0.25 g, 0.7 mmol) in methanol (10 ml) was added a catalytic amount of palladium (5% on activated carbon). The resultant mixture was hydrogenated at ambient pressure until the hydrogen uptake had ceased, whereafter it was filtered through celite. The filtrate was evaporated under reduced pressure to afford the desired product, quantitatively.

2-Amino-4-cyclohexyl-N-(3-(1-pyrrolyl)phenyl)aniline is prepared analogously from 4-cyclohexyl-N-(3-(1-pyrrolyl)phenyl)-2-nitroaniline.

2-Amino-4-cyclohexyl-N-(3-(1-pyrazolyl)phenyl)aniline is prepared analogously from 4-cyclohexyl-N-(3-(1-pyrazolyl)phenyl)-2-nitroaniline.

5-Cyclohexyl-1-(3-(1-imidazolyl)phenylbenzimidazole, hydrochloride. A solution of 2-amino-4-cyclohexyl-N-(3-(1-imidazolyl)phenyl)aniline (0.2 g, 0.6 mmol) in formic acid (1 ml) was stirred at reflux for 4 hours. The cooled mixture was rendered alkaline by addition of aqueous sodium hydroxide (6M) and extracted with ethyl acetate. The organic extract was dried over magnesium sulphate, concentrated under reduced pressure and eluted through silica gel with a mixture of ethyl acetate and ethanol (4:1, v/v). The desired product precipitated as the hydrochloride upon addition of etheral hydrogen chloride to the eluate. (0.1 g) Mp 222-225° C.

5-Cyclohexyl-1-(3-(1-pyrrolyl)phenyl)benzimidazole is prepared analogously from 2-amino-4-cyclohexyl-N-(3-(1-pyrrolyl)phenyl)aniline.

5-Cyclohexyl-1-(3-(1-pyrazolyl)phenyl)benzimidazole is prepared analogously from 2-amino-4-cyclohexyl-N-(3-(1-pyrazolyl)phenyl)aniline.

Test Methods

Test Method 1

In Vitro Inhibition of $^3$H-flunitrazepam ($^3$H-FNM) Binding

The GABA recognition site and the benzodiazepine modulatory unit can selectively be labelled with $^3$H-flunitrazepam.

Tissue Preparation

Preparations are performed at 0-4° C. unless otherwise indicated. Cerebral cortex from male Wistar rats (150-200 g) is homogenised for 5-10 sec in 20 ml Tris-HCl (30 mM, pH 7.4) using an Ultra-Turrax homogeniser. The suspension is centrifuged at 27,000×g for 15 min and the pellet is washed three times with buffer (centrifuged at 27,000×g for 10 min). The washed pellet is homogenized in 20 ml of buffer and incubated on a water bath (37° C.) for 30 min to remove endogenous GABA and then centrifuged for 10 min at 27,000×g. The pellet is then homogenized in buffer and centrifuged for 10 min at 27,000×g. The final pellet is resuspended in 30 ml buffer and the preparation is frozen and stored at −20° C.

Assay

The membrane preparation is thawed and centrifuged at 2° C. for 10 min at 27,000×g. The pellet is washed twice with 20 ml 50 mM Tris-citrate, pH 7.1 using an Ultra-Turrax homogeniser and centrifuged for 10 min at 27,000×g. The final pellet is resuspended in 50 mM Tris-citrate, pH 7.1 (500 ml buffer per g of original tissue), and then used for binding assays. Aliquots of 0.5 ml tissue are added to 25 µl of test solution and 25 µl of $^3$H-FNM (1 nM, final concentration), mixed and incubated for 40 min at 2° C. Non-specific binding is determined using Clonazepam (1 µM, final concentration). After incubation the samples are added 5 ml of ice-cold buffer and poured directly onto Whatman GF/C glass fibre filters under suction and immediately washed with 5 ml ice-cold buffer. The amount of radioactivity on the filters is determined by conventional liquid scintillation counting. Specific binding is total binding minus non-specific binding.

Results 25-75% inhibition of specific binding must be obtained, before calculation of an $IC_{50}$.

The test value will be given as $IC_{50}$ (the concentration (µM) of the test substance which inhibits the specific binding of $^3$H-FNM by 50%).

$$IC_{50} = \text{(applied test substance concentration, } \mu\text{M)} \times \frac{1}{\left(\frac{C_o}{C_x} - 1\right)}$$

where
$C_o$ is specific binding in control assays, and
$C_x$ is the specific binding in the test assay.
(The calculations assume normal mass-action kinetics).

What is claimed is:

1. A compound of the Formula I:

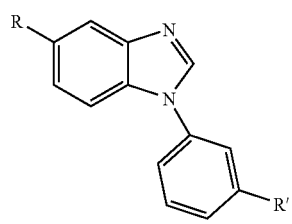

(I)

or an N-oxide thereof, or any of its stereoisomers or any mixture of its stereoisomers, or a pharmaceutically acceptable salt thereof, wherein R represents cyclopropyl; and R' represents a 5-7-member heterocyclic ring;

which heterocyclic ring may optionally be subsituted one or more substituents independently selected from the group consisting of with halo, hydroxy, amino, alkylamino, aminoalkyl, alkylaminoalkyl, cyano, nitro, trifluoromethyl, trifluoromethoxy, alkoxy, alkoxyalkyl, cycloalkoxy, alkyl, cycloalkyl, cycloalkylalkyl, alkenyl, and alkynyl.

2. The compound of claim 1, wherein R' represents a heterocyclic ring selected from the group of pyridyl, thiazolyl, isoxazolyl, imidazolyl, pyrrolyl and pyrazolyl, which heterocyclic ring may optionally be substituted with one or more halo.

3. The compound of claim 1, which is

5-Cyclopropyl-1-(3-(3-pyridyl)phenyl)benzimidazole;

5-Cyclopropyl-1-(3-(2-thiazolyl)phenyl)benzimidazole;

5-Cyclopropyl-1-(3-(2-fluoro-5-pyridyl)phenyl)benzimidazole;

5-Cyclopropyl-1-(3-(3-isoxazolyl)phenyl)benzimidazole;

5-Cyclopropyl-1-(3-(1-oxy-3-pyridyl)phenyl)benzimidazole;

or an N-oxide thereof, or any of its stereoisomers or any mixture of its stereoisomers, or a pharmaceutically acceptable salt thereof.

4. A pharmaceutical composition, comprising a therapeutically effective amount of a compound of claim 1, or an N-oxide thereof, or any of its stereoisomers or any mixture of its stereoisomers, or a pharmaceutically acceptable salt thereof, together with at least one pharmaceutically acceptable carrier, excipient or diluent.

5. A method for treatment, or alleviation of anxiety, convulsions or sleep disorders in a living animal body, which method comprises the step of administering to said living animal body in need thereof a therapeutically effective amount of a compound according to claim 1, or an N-oxide thereof, or any of its stereoisomers or any mixture of its stereoisomers, or a pharmaceutically acceptable salt thereof.

6. The method for the manufacture of a pharmaceutical composition, comprising incorporating the compound of Formula I as recited in claim 1 or an N-oxide thereof, or any of its stereoisomers or any mixture of its stereoisomers, or a pharmaceutically acceptable salt thereof into a pharmaceutically acceptable carrier selected from the group consisting of powders, tablets, pills, capsules, cachets, suppositories, dispersible granules, solutions, suspensions and emulsions.

7. The method according to claim 5, wherein said living animal body is a human.

* * * * *